United States Patent [19]

Descoins et al.

[11] 4,169,879
[45] Oct. 2, 1979

[54] REACTOR SUITABLE FOR CHEMICAL REACTIONS BRINGING FLUIDS INTO ACTION IN CONTACT WITH A BED OF SOLIDS

[75] Inventors: Daniel Descoins, Salins; Alain Portes, Cauffry; Pierre Lafon, St. Avold, all of France

[73] Assignee: Societe Chimique des Charbonnages, Courbevoie, France

[21] Appl. No.: 835,081

[22] Filed: Sep. 20, 1977

[30] Foreign Application Priority Data

Sep. 22, 1976 [FR] France ................................ 76 28540

[51] Int. Cl.² .......................... B01J 8/02; C07C 15/09; C07C 15/10; C07B 3/00
[52] U.S. Cl. .................................... 422/220; 260/696; 422/218; 585/441; 585/922; 585/925
[58] Field of Search ............................. 23/288 R, 289; 260/669 R, 696

[56] References Cited

U.S. PATENT DOCUMENTS

| 2,635,989 | 4/1953 | Bonner | 23/288 R X |
|---|---|---|---|
| 2,639,224 | 5/1953 | McAfee | 23/288 R |
| 2,886,517 | 5/1959 | Patton et al. | 23/288 R X |
| 2,997,374 | 8/1961 | Lavender, Jr. et al. | 23/288 R |
| 3,027,244 | 3/1962 | Byrne et al. | 23/288 R |
| 3,051,561 | 8/1962 | Grimes | 23/288 R |
| 3,167,399 | 1/1965 | Hansen, Jr. | 23/288 R |
| 3,211,537 | 10/1965 | Groebe et al. | 23/288 R |
| 3,235,343 | 2/1966 | Riggins | 23/288 R |
| 3,515,763 | 6/1970 | Uitti | 260/669 R |

*Primary Examiner*—Joseph Scovronek
*Attorney, Agent, or Firm*—Karl W. Flocks

[57] ABSTRACT

The reactor is traversed by a central tube with an essentially radial circulation of the gases or other fluids. Said cylindrical part of the solids bed is surmounted by a substantially hemispherical reaction zone permeable to said gases or other fluids. The hemispherical part of the reactive zone is comprised between two substantially hemispherical caps one of which surmounts the central tube and the other bounds the upper periphery of this zone with the pressure drop undergone by the gases or other fluids passing through the hemispherical zone being greater than that undergone by the gases or other fluids passing through the cylindrical zone and therefore the perforations of the hemispherical part of the central tube are calculated to compensate for this difference and equalize the flow of gases or other fluids in the whole of the solids mass.

7 Claims, 2 Drawing Figures

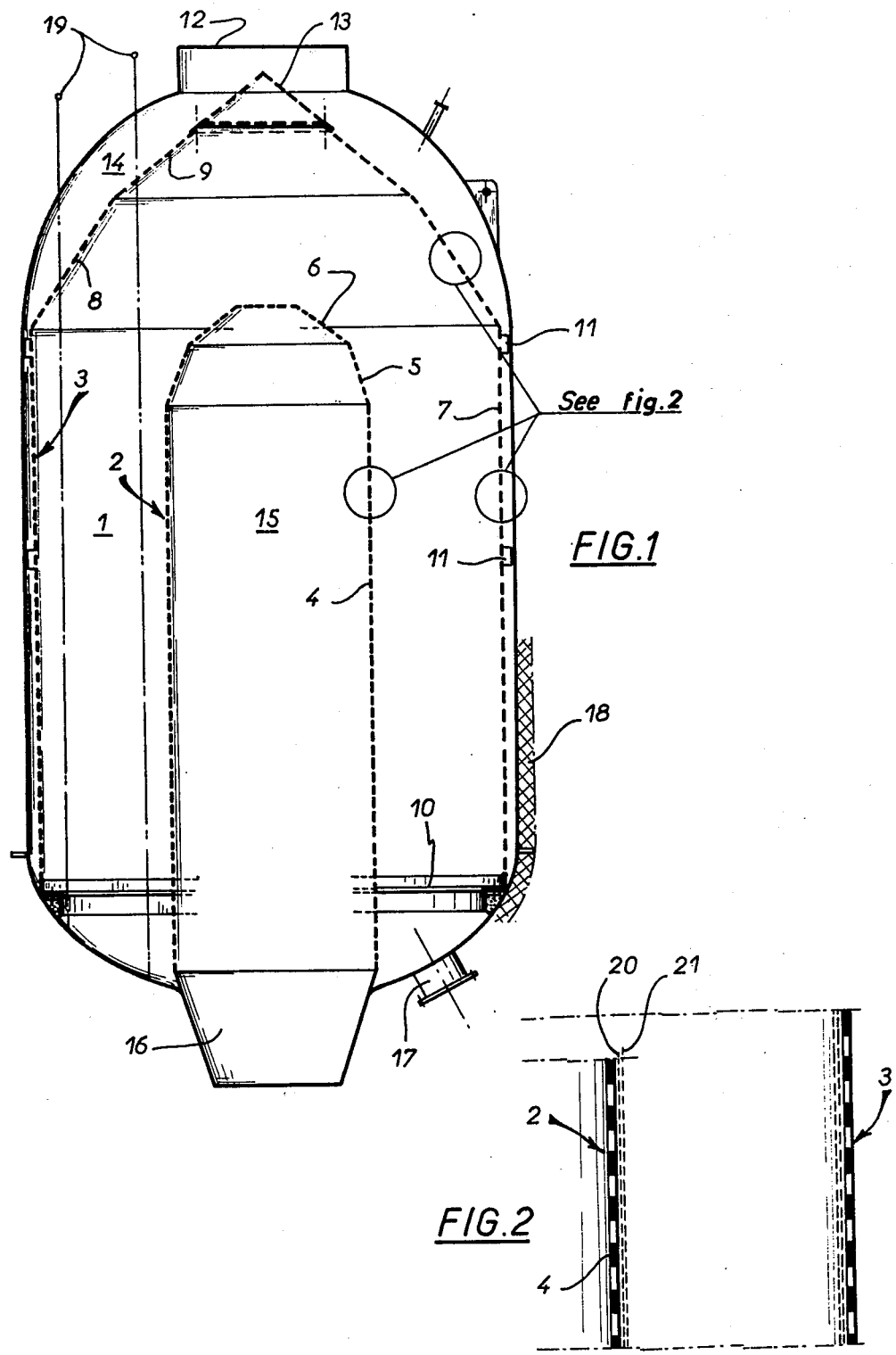

4,169,879

REACTOR SUITABLE FOR CHEMICAL REACTIONS BRINGING FLUIDS INTO ACTION IN CONTACT WITH A BED OF SOLIDS

BACKGROUND OF THE INVENTION

1. Field of the Invention

The present invention relates to an improved reactor suitable for chemical reactions bringing into play fluids in contact with a bed of solids. This is notably the case in reactors lined with a bed of solids traversed by the one or more fluids to be reacted.

2. Description of the Prior Art

Thus for example reactions for the dehydrogenation of hydrocarbons and in particular the manufacture of styrene from ethylbenzene are customarily carried out by passing a superheated mixture of hydrocarbon and steam through a catalyst bed placed inside a cylindrical reactor. In the reactor, the gas circulation can be effected parallel to the axis for the cylinder, the reactor then being called axial, or parallel to the radii of cross sections of the cylinder, the reactor then being called radial. The design of reactors of greater and greater capacity has led to the gradual abandonment of axial reactors in favour of radial reactors.

In radial reactors, the circulation of the gases or other fluids can be carried out either from the middle of the reactor to the periphery, the reactor then being called centrifugal, or from the periphery to the axis of the reactor, the reactor being called in this case centripetal.

Centrifugal reactors are sometimes preferred, since they offer the gases or other fluids a lower pressure drop, which favors the selectivity of the reaction and consequently the yield. However centripetal reactors possess various advantages which may render them preferable to centrifugal reactors: their technological construction is easier; on the other hand, superheated intake fluids are placed in contact with the largest surface of the solid material, which diminishes the risk of fouling and ensures better distribution of the fluids in the solid mass; finally the largest empty space of the reactor which is necessarily the central tube is kept at the lowest temperature.

In radial reactors, a gradual packing of the bed of solid material occurs in the course of its use. To compensate this packing and to maintain correct radial circulation in the reactor, it is necessary to place an excess of solid material in the upper portion of the reactor. It has already been proposed to replace this excess material, at least in part, by an inert substance, but it is then observed that this inert substance penetrates little by little into the whole of the principal bed resulting in poor utilisation of the latter. On the other hand, this upper portion of the bed, whatever its composition, gradually fouls, since it is not swept by the reaction gases or other fluids.

It is an object of the present invention to enable these drawbacks to be overcome by providing a type of reactor with an essentially radial circulation in which the whole of the solid mass is traversed by the reaction gases or other fluids.

GENERAL DESCRIPTION OF THE INVENTION

The reactor according to the invention is characterized by the fact that the cylindrical part of the bed of the solid material is surmounted by a substantially hemispherical reactive zone.

From the technological point of view, rather than to form spherical surfaces, it is sometimes easier to construct an assembly of cylindrical and frustoconic elements which are inscribed within a sphere. This is why the expression "substantially hemispherical", which encompasses such surfaces, is employed.

The substantially hemispherical reactive zone is preferably comprised between two substantially hemispherical calottes or caps, the inner cap surmounting the central tube of the reactor.

Within the substantially hemispherical zone, the circulation of the gases or other fluids is effected along the radii of the sphere.

The circulation of the gases or other fluids in the reactor according to the invention may be centrifugal or centripetal. It is preferably centripetal.

In such a reactor, the flow resistance of the product increases in proportion as the product moves towards the center. Thus, the pressure drop per unit length is low in the peripheral zone of the bed and much higher in the part neighbouring the center. As a result a decrease in the level of the solid bed in the upper portion of the reactor, due to packing, has only a slight influence on the pressure drop and consequently on the circulation of the gases or fluids in the reactive mass.

The solid reaction mass is, in manner known in itself, kept in place by means of one or several thicknesses of grating. In addition, according to the invention, between this mass and the empty parts of the reactor, is inserted a perforated metal sheet whose purpose is, on the one hand to keep this solid mass in position, and on the other hand, to ensure an additional non-negligible pressure drop of the order of 0.5 to 12%, advantageously from 1 to 6% of the pressure drop created by the solids bed proper. This pressure drop enables the realization of a better distribution of the gases or other fluids within the mass. It has also the purpose of reducing to the minimum the effect of the variation in pressure drop in the upper portion of the reactor consequent upon packing of the bed of solid material.

Thus, in a reactor according to the invention, the mass of solid material is separated from the empty part situated at the periphery of the reactor by a perforated metal sheet ensuring a predetermined pressure drop. This mass is also separated from the central tube by a perforated metal sheet.

The substantially hemispherical part and the cylindrical part of the central tube include different perforations. In fact, the pressure drop undergone by the gases or other fluids passing through the hemispherical zone is greater than that undergone by the gases or other fluids which pass through the cylindrical zone. Hence the perforations of the hemispherical part of the central tube are calculated, so as to compensate for this difference. The calculation takes into account an average packing of the solids bed in its upper part.

BRIEF DESCRIPTION OF THE DRAWINGS

Other characteristics and advantages of the invention will emerge more clearly from the description which follows taken in conjunction with the accompanying drawings in which:

FIG. 1 shows, by way of example, a sectional view of one embodiment of a centripetal circulating reactor according to the invention, used for catalytic dehydrogenation and notably for dehydrogenation of ethylbenzene into styrene; and FIG. 2 shows, on a larger scale a detail of the embodiment of FIG. 1.

DESCRIPTION OF A PREFERRED EMBODIMENT

The reactor comprises a catalytic mass 1 included between a perforated metal sheet 2 defining the central tube 15 of the reactor and a perforated metal sheet 3 separating the catalytic mass from the peripheral empty portion 14 of the reactor. The perforated metal sheet 2 comprises a cylindrical element 4 surmounted by two frustoconic portions 5 and 6 which define a substantially hemispherical zone. The perforations of the cylindrical element 4 represent 8% of its surface (pressure drop about 5 g/cm$^2$), whilst the perforations of the frustoconic portions 5 and 6 represent about 16% of their surface (pressure drop of about 1 g/cm$^2$). The perforated metal sheet 3 comprises similarly a cylindrical element 7 surmounted by two frustoconic portions 8 and 9. The perforations of the metal sheet 7 represent 3% of its surface (pressure drop about 8 g/cm$^2$). The perforations of the metal sheets 8 and 9 represent about 3% of its surface (pressure drop about 5 g/cm$^2$). The mass of the catalyst is separated from the metal sheets 2 and 3 by two metallic gauzes 20–21 (FIG. 2) the first 20 with large meshes applied to the perforated metal sheet on the catalytic bed side, enabling the distribution of the gases between the perforations of the metal sheet, the second 21, with small meshes, applied on to the first holding the catalytic bed and preventing obstruction of the perforations. The mass of catalyst rests on a support 10 designed so as to permit, in known manner, the free expansion of the reactor. The centering elements 11 ensure the sound positioning of the mass of catalyst.

The superheated reaction gases are introduced into the reactor through the aperture 12. A perforated sheet metal cone 13 ensures the distribution of the gases in the peripheral empty space 14 before their entry into the catalyst mass. The gases pass through the catalytic mass thereby becoming cooled, the dehydrogenation reaction being endothermic, they reach the central tube 15 and energe through the aperture 16.

The reactor includes also openings 17 for the emptying of the catalyst, an external insulation 18, and temperature and pressure sockets 19.

It is self-evident that the present invention has been described in only a manner which is purely explanatory and in no way limiting and that any useful modification at the level of equivalents could be introduced without departing from its scope as defined by the appended claims.

We claim:

1. Reactor for bringing gases or other fluids into contact with a bed of solid catalyst material comprising means to move the gases or other fluids in an essentially radial direction of flow including
    a central perforated tube inside the reactor,
    a perforated means enclosing the bed of solid catalyst material comprising a cylindrical bed forming means with a substantially hemispherical reaction zone permeable to the gases or other fluids surmounting said cylindrical bed forming means and formed in between two perforated substantially hemispherical caps,
    one of said caps surmounting said central perforated tube,
    the other of said caps bounding the upper periphery of the bed of catalyst material.

2. Reactor according to claim 1, wherein said central peforated tube is constituted by a perforated metal sheet.

3. Reactor according to claim 2, wherein said perforated cylindrical means forming the cylindrical bed and said substantially hemispherical cap have different pressure drops per unit surface so as to equalize the flow of the gases or other fluids in the whole of the solids mass.

4. Reactor according to claim 3, wherein the pressure drops therethrough are distributed therein in the following manner with
    said central perforated tube having a pressure drop of about 5 g/cm$^2$,
    said one of said caps surmounting said central perforated tube having a pressure drop of about 1 g/cm$^2$,
    said other of said caps bounding the upper periphery of the bed of catalyst material having a pressure drop of about 5 g/cm$^2$,
    and said means to form a cylindrical bed enclosing the bed of solid catalyst material including a peripheral cylindrical element having a pressure drop of about 8 g/cm$^2$.

5. Reactor according to claim 1, wherein
    said other of said caps bounding the upper periphery of the bed of catalyst material comprises a metal sheet with non-negligible pressure drop.

6. Reactor according to claim 5, wherein said non-negligible pressure drop is of the order of 0.5 to 12%, of the pressure drop created by the solids bed proper.

7. Reactor according to claim 6, wherein said non-negligible pressure drop is from 1 to 6% of the pressure drop created by the solids bed proper.

* * * * *